United States Patent [19]
Cranage

[11] 3,965,903
[45] June 29, 1976

[54] SUCTION BOTTLE ASSEMBLY

[75] Inventor: Bidwell Chapman Cranage, Ferguson, Mo.

[73] Assignee: Chemetron Corporation, Chicago, Ill.

[22] Filed: May 23, 1975.

[21] Appl. No.: 580,496

[52] U.S. Cl. .............................. 128/276; 73/317; 137/445
[51] Int. Cl.² ......................................... A61M 1/00
[58] Field of Search ........................ 128/275–278; 215/311; 251/231; 137/409, 434, 442, 445; 141/198, 205; 222/556–557; 73/317

[56] References Cited
UNITED STATES PATENTS

| | | | |
|---|---|---|---|
| 2,079,412 | 5/1937 | Justus | 137/445 X |
| 2,427,359 | 9/1947 | Koenhold, Sr. | 251/231 X |
| 3,620,408 | 11/1971 | Holbrook | 128/277 |
| 3,685,517 | 8/1972 | Reynolds et al. | 128/277 |
| 3,768,478 | 10/1973 | Fertik et al. | 128/276 |
| 3,805,788 | 4/1974 | Kleiner | 128/276 |
| 3,878,962 | 4/1975 | Holbrook et al. | 128/276 |

*Primary Examiner*—Robert W. Michell
*Assistant Examiner*—Henry S. Layton
*Attorney, Agent, or Firm*—N. M. Esser

[57] ABSTRACT

A suction bottle assembly for effecting drainage from a patient. The assembly has a float, which is responsive to the level of drainage in the bottle, that is connected to the cover by a preferably parallel bar bracket. The bracket causes the float to rise substantially vertically and also seals off the vacuum inlet and opens a vacuum relief valve to create a pressure balance within the bottle with the outside atmospheric pressure, thus preventing overflow.

10 Claims, 7 Drawing Figures

SUCTION BOTTLE ASSEMBLY

BACKGROUND OF THE INVENTION

1. Field of the Invention

This invention pertains to medical suction bottle assemblies.

2. Description of the Prior Art

Medical suction bottle assemblies in general use consist of a bottle and cover which are secured together with a leak tight fit. Two connections are provided in the cover, one to be connected by hose or other means to the source of vacuum, for example, a vacuum pump or hospital vacuum outlet station, the other connection being connected by means of a hose to the particular area in a patient requiring drainage.

There is normally a float assembly in line with the vacuum source inlet that will close off same as the float rises to a predetermined level. Floats mounted on stems guided by bushing have been used, the stem having a disc or seal at the upper end to effect a shut-off of the vacuum source. In other cases the float may be enclosed in a vertical cage, the float itself acting as the plug to seal the inlet. In still other cases, flapper type shut-off valves have been used.

In all of the above cases, at the moment of shut-off a residual vacuum or negative pressure exists in the bottle. Flow will continue from the patient until this negative pressure is in balance with the atmospheric pressure less the weight of the column of fluid still in the patient.

Medically, various negative pressures are used and to avoid contamination of the suction lines the float level for shut-off must be kept low in the jar, resulting in great inefficiency of volumetric use.

Reliance on a float operated vacuum source shut-off valve alone has resulted in contamination of equipment when shut-off leakage has occurred. Hence providing an apparatus to effectively seal off the vacuum source and vent the negative pressure to conclude the drainage operation is important.

SUMMARY OF THE INVENTION

Applicant has designed a suction bottle assembly that generally avoids the problems of the prior art. Specifically Applicant has designed an integral bracket of preferably polypropylene which has a pair of parallel bars each of which is hingedly mounted on the cover and has a member hingedly mounted therebetween at their other ends. The member has an extension which is connected to an open bottom float. The upper bar has a cantilever supported, and therefore flexible, sealing surface between its mounting on the cover and the member, that is adapted to contact the opening for the inlet vacuum located in the cover. The upper bar also is constructed to engage a vacuum relief valve located in the cover for the purpose of venting the bottle to atmosphere at substantially the same time as the bracket sealing surface closes the vacuum inlet as the float rises and to close the vacuum relief valve when the float drops and the vacuum inlet is opened.

A feature of the parallel bar bracket is the essentially resulting vertical motion of the float for reduced bottle size and efficient float and bracket action. The bracket is designed so that it can be molded or fabricated in essentially one plane and when folded, being flexed on the four flexible hinge areas, becomes a one piece parallel bar mechanism. The afore mentioned cantilever sealing surface provides flexibility, so that after the initial sealing of the vacuum inlet occurs, and during the period that the float is still rising, until the vacuum breaker valve has opened to relieve the negative pressure in the bottle, the seal can modify its position with respect to the angular motion of the upper parallel bar and still maintain a seal.

The float, although connected to the member beyond the vacuum inlet, which is preferably located in the center of the cover, preferably has its centerline substantially close to the centerline of the bottle for efficient use of the bottle space. Due to the rather large size float needed to secure sufficient mechanical advantage to open the relief valve and the desire to keep same remote from the drainage intake, the float is larger in a direction transverse to the bracket than parallel to same. An open bottom float is also preferred so that there will be no collapse of the thin wall structure under vacuum conditions.

While the entire suction bottle assembly could be reusable if sterilized, all components are preferably economically constructed of plastic and thus disposable after use. The upper peripheral edge of the bottle has a taper fit with a thin annular lip in the cover which can flex as the bottle is urged into the cover. Vacuum conditions in the bottle when in use aid in creating a tight seal as the thin lip tends to flex inwardly.

It is, therefore, an object of this invention to provide a new and improved suction bottle assembly.

Another object of this invention is to provide a suction bottle assembly with a parallel bar bracket, which when actuated by a vertically movable float, will effectively seal off the vacuum inlet in a bottle of compact configuration and open a relief valve to vent the bottle to atmospheric pressure and stop the drainage operation.

Another object of this invention is to provide a suction bottle assembly with a parallel bar bracket actuated by an open bottom float that is raised by the pressure of the gas which may be foam trapped therein.

DESCRIPTION OF THE PREFERRED EMBODIMENT

Figure 1:
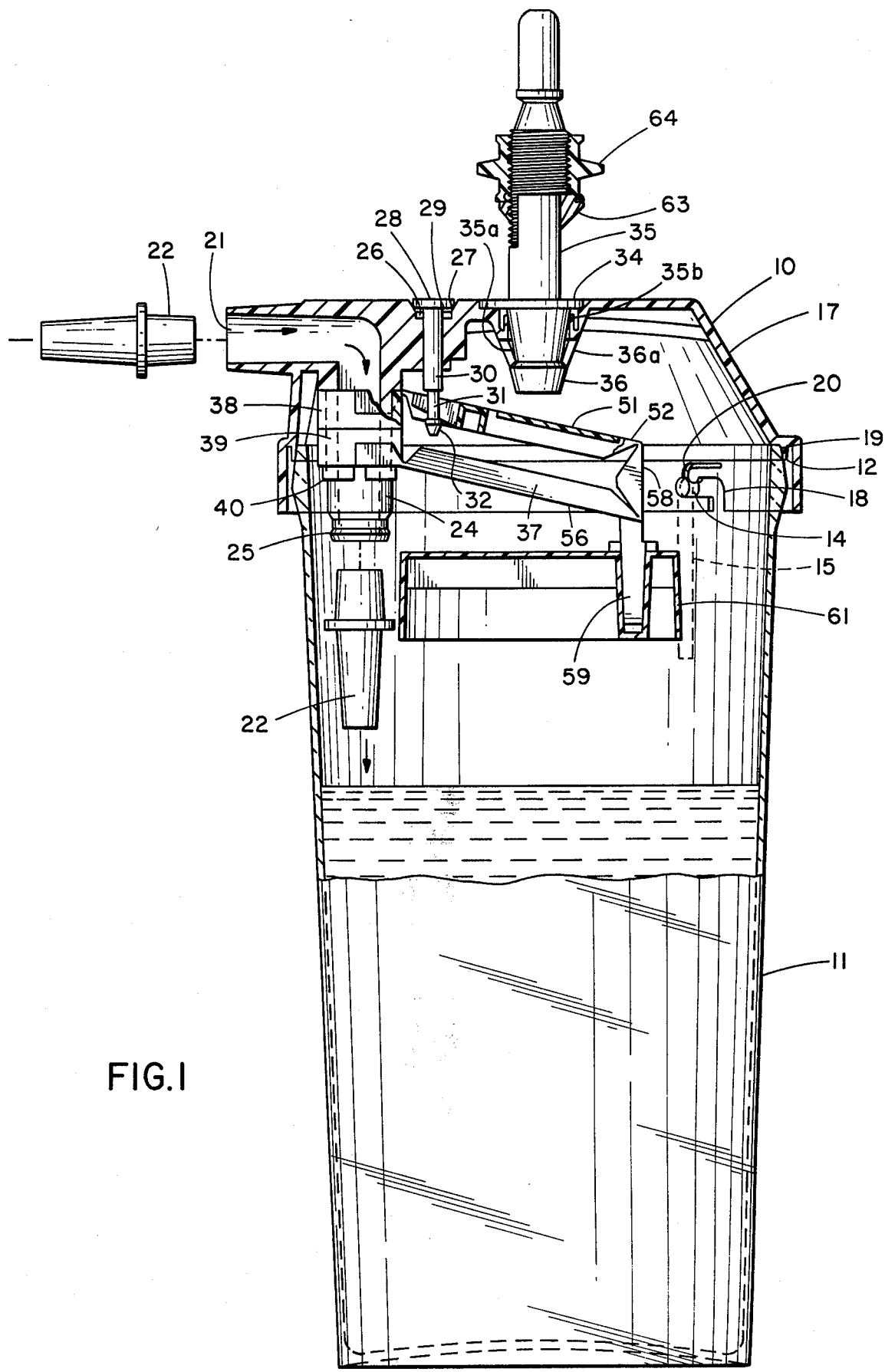
FIG. 1 is a partial sectional elevational view of a suction bottle assembly with the components in the position in which drainage is moving into the bottle.

Referring to FIG. 1, 10 indicates the suction bottle assembly of this invention. Assembly 10 includes bottle 11, which may be made of impact resistant, clear polystyrene. Bottle 11 has an elongated, slightly tapered configuration with a tapering and curved lip 12. Also a part of bottle 11 are four equally spaced, generally circular lugs 14. Each lug 14 has a longitudinally extending reinforcing rib 15 which is also used to limit stacking. Suitable graduations may be shown on the bottle for indicating the amount of drainage in the bottle.

Bottle 11 is preferably connected to cover 17 by means of the aforesaid lugs 14. Cover 17 has suitable spaced slots 18 for lugs 14. Each slot has a cammed configuration that extends generally transverse to the center line of the bottle 11 and which forces each lug 14 entering therein, to draw the tapered cover sealing surface 19 tightly against lip 12 of bottle 11. Due primarily to the flexibility of cover 17, which may be made of white polypropylene or high density polyethylene, an air tight seal is provided between surface 19 and lip 12 without the need of the special seal. Also a part of the cover is flexible bead 20 adjacent the slot 18 which maintains the lug in the slot until separation of the cover and bottle is desired.

Cover 17 also has an opening 21 extending from its inside surface outwardly. Opening 21 has a suitable plastic which may be acetal hose nipple 22 adapted to be mounted therein and having a tapered configuration adapted to be connected to a hose extending to a patient from which drainage is to be effected. Nipple 22 has a tapered end to provide an air-tight fit with the opening 21. Nipples 22 are provided to permit optional use of smaller diameter hose from the patient and also to channel flow to the bottom of the bottle. Opening 21 extends from the outside surface of the cover and preferably into the bottle and has a configuration for second, similar hose nipple 22. Located above second hose nipple 22, opening 21 has an external peripheral surface 24 which is suitably tapered for a later to be described purpose and has a recessed end 25 for securing nipple 22 in opening 21. Opening 21 along with nipples 22 constitutes an intake means for drainage from a patient.

Cover 17 also has an aperture 26 defined by a seat 27 for plug type vacuum relief valve 28 extending therethrough. Plug valve 28 may be made of thermo plastic material. Valve 28 has a head 29 for contacting seat 27 and an elongated shaft portion 30 extending into the interior of cover 17. Also a part of valve 28 is reduced portion 31 and end 32.

Preferably located in the top and center thereof of cover 17, is inlet 34. Inlet 34 preferably contains stem 35 which may be made from polypropylene. Stem 35 extends through inlet 34 and has a tapered surface 35a engaging a complementary surface or lip 35b in inlet 34 for an air-tight fit therewith similar to the fit between cover 17 and bottle 11. Stem 35 has a head 36 providing the shut-off valve surface. The conical shape of head 36 spreads four tapered lugs 36a in the cover which snap into 35a to secure inlet 34 to cover 17. Head 36 defines an opening for the application of vacuum therethrough to the bottle assembly via the stem. Stem 35 and inlet 34 provide an inlet means for a vacuum.

Figure 2:
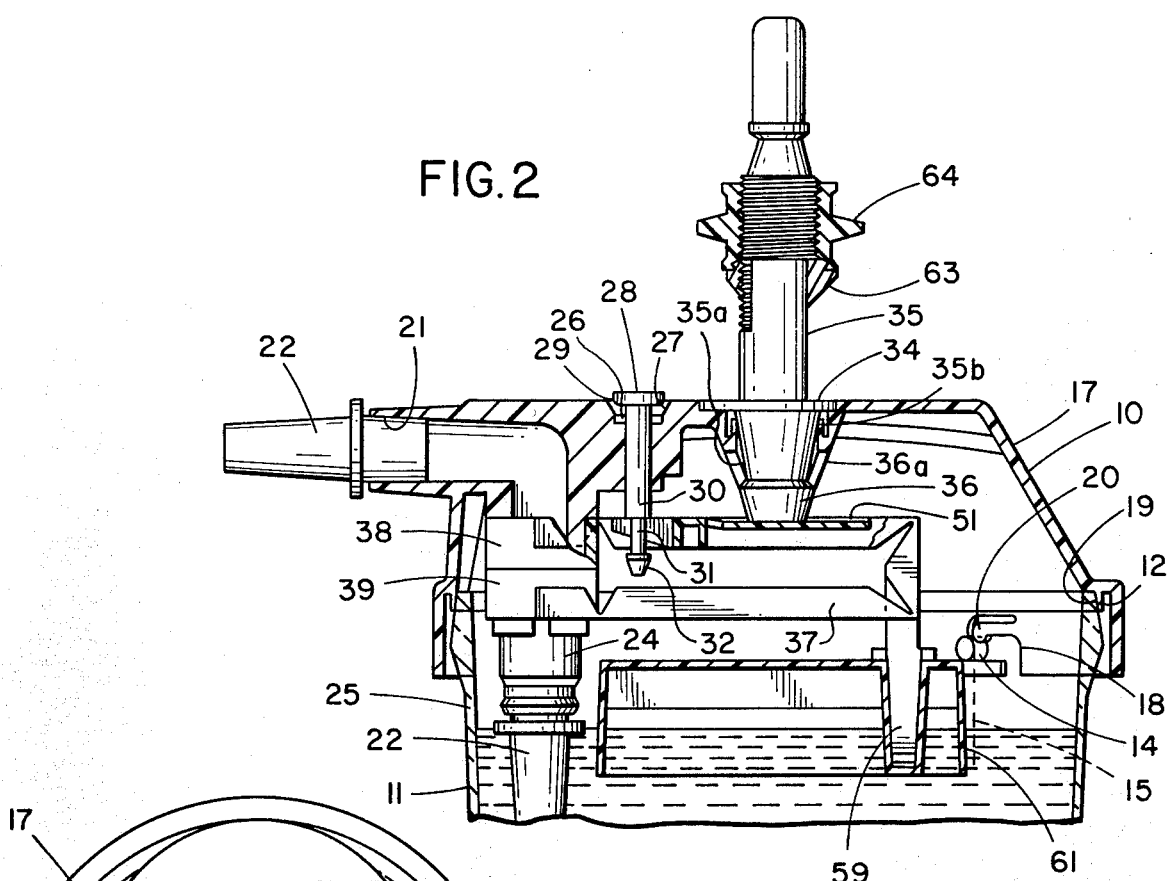
FIG. 2 is a view similar to FIG. 1 with the float and related components in the raised position and the vacuum inlet closed and the vacuum relief valve open, stopping the drainage operation.
Figure 3:
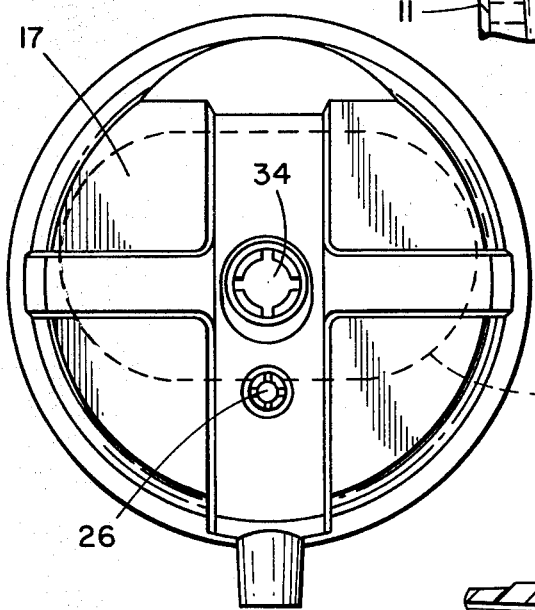
FIG. 3 is a plan view of the suction bottle assembly with the float shown in the raised position in broken lines.
Figure 7:
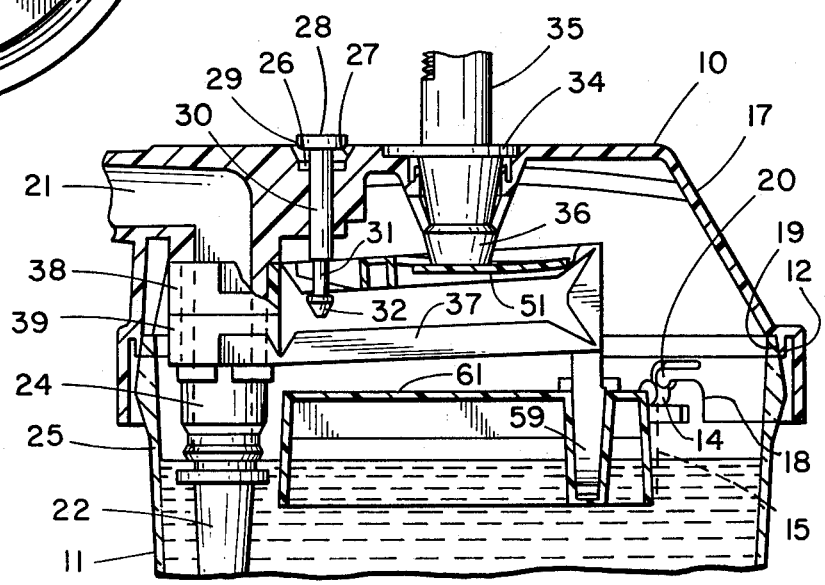
FIG. 7 is a view similar to FIG. 2, showing the float and bracket in the overflow condition.
Figure 4:
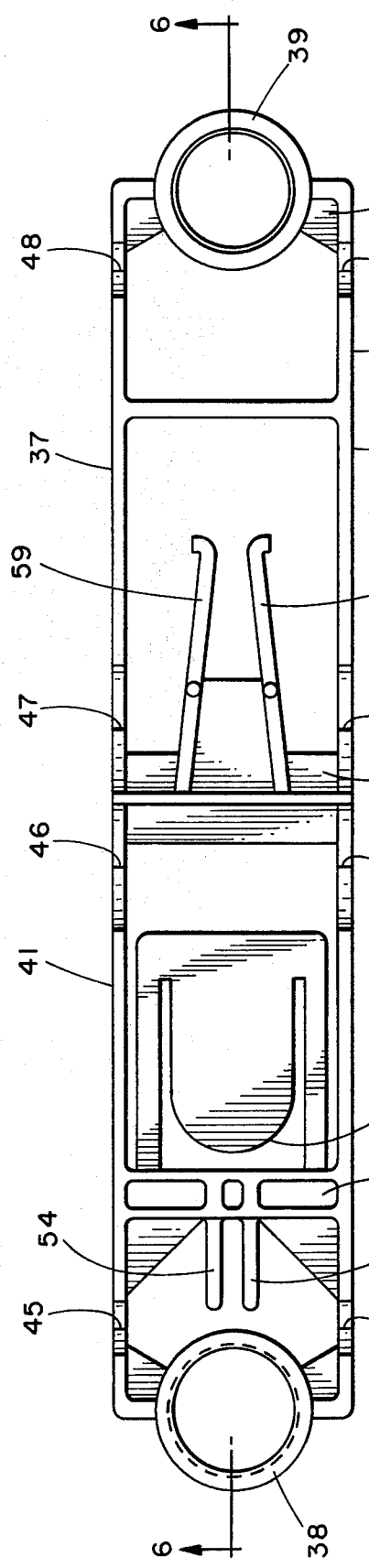
FIG. 4 is a plan view of the bracket of the assembly in the unfolded position.
Figure 5:
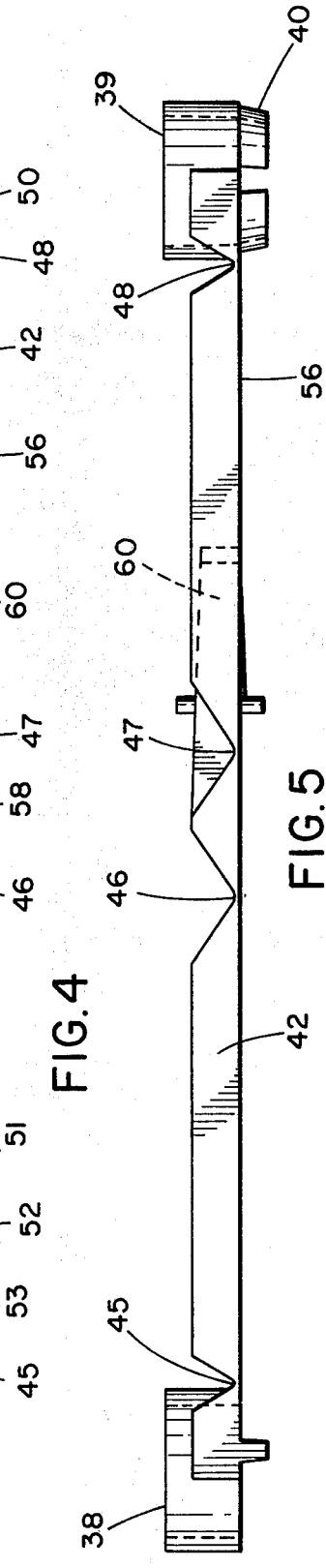
FIG. 5 is a front view of the bracket.
Figure 6:
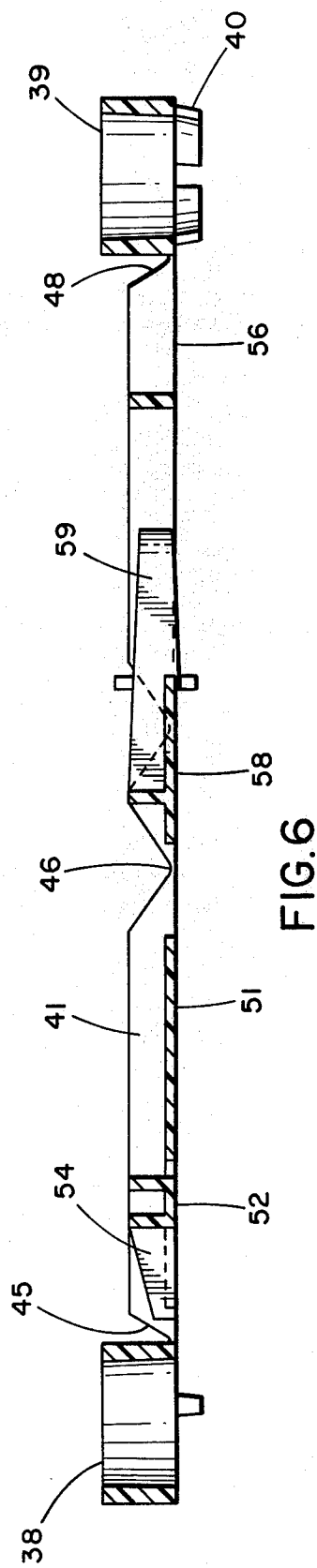
FIG. 6 is a sectional view taken along line 6—6 of FIG. 5.

Bracket 37, shown in the folded position in FIGS. 1, 2 and 7, is shown in detail in FIGS. 4 through 6. Bracket 37 is preferably molded as an integral, elongated unit from polypropylene. As shown in FIG. 4, Bracket 37 has tapered and hollow mounting bosses 38 and 39 at each end thereof. In the folded position bosses 38 and 39 are aligned and are adapted to be mounted on peripheral surface 24 surrounding opening 21 in cover 17. Slotted and tapered legs 40 provide a tight grip on surface 24 securely maintaining bosses 38 and 39 thereon. Bracket 37 also has longitudinally extending side walls 41 and 42 which connect the bosses 38 and 39. Each wall has spaced and aligned V shaped slots which define (with the material remaining) flexible hinges or fold points 45, 46, 47 and 48. Bottom wall 50 extends the length of the bracket and between side walls 41 and 42. Wall 50 has suitable reinforcements and cut out portions as needed. Specifically, wall 50 has cantilever supported and thus flexible sealing portion 51 which is polished and molded free of imperfections and which is adapted to contact and close the vacuum inlet 34. Portion 51 is in what may be denominated the upper bar 52 of the bracket in the folded position. Upper bar 52 also has ribs 53 and slot 54 therebetween adjacent boss 38. Slot 54 is constructed for the passage therethrough of portion 31 of valve plug 28. End 32 and shaft portion 31 cannot pass through slot 54 which thereby maintains valve plug 28 in bracket 37. Lower bar 56 is also a part of bottom wall 50. Connecting upper bar 52 and lower bar 56 by means of hinges 46 and 47 is member portion 58. Member portion 58 has a pair of arms 59 and 60 extending generally parallel thereto. In the folded position as shown in FIG. 1, arms 59 and 60, are connected to open bottom, generally oblong shaped float 61 as shown in FIG. 3 and FIGS. 1 and 2. Float 61 has suitable recesses in which the ends of arms 59 and 60 resiliently engage. Float 61 is made of a rigid impact resistant thermoplastic material.

Suction bottle assembly 11 may be supported at a conventional outlet (not shown) by means of a polypropylene cone 63 which is constructed to be snapped on stem 35 and also engaged by a thermoplastic holding nut 64, having peripheral lugs, threaded on stem 35 and also engaging a thread on cone 63. Suitable fittings (not shown) such as a Diameter Index Safety System (DISS) nut and threaded hose adapted can be provided to detachably connect the end of stem 35 to a source of vacuum. Alternately, a hose adapter stem may be used in lieu of stem 35 and similarly connected to cover 17. A suitable smaller suction hose nipple can be used therewith.

In operation, with the suction bottle assembly 10 shown as in FIG. 1 with the hose nipple 22 connected to a suitable hose extending to a patient and vacuum applied to stem 35, fluid and air will flow through opening 21 into bottle 11. It is to be noted that plug valve 28 is closed and supports bracket 27 and float 61 in the lowered position. Also vacuum assists in maintaining valve 28 in the closed position. As the bottle gradually fills, float 61 will rise, generally vertically, moving bracket 27 about hinges 45, 46, 47 and 48 until upper bar 52 portion 51 contacts vacuum inlet 34 closing same (see FIG. 2). Approximately at the same time plug valve 28 has been lifted by bracket 37 until head 29 has been lifted from seat 27, thereby venting bottle 11 to the atmosphere. At some point, when the bottle has reached substantially atmospheric pressure the drainage flow to the bottle will stop. Before this point has been reached any overflow will continue to force float 61 and therefore bracket 37 upward. Due to the flexible bracket and flexible hinges upper bar 52 and portion 51 will fold about vacuum inlet 34 as upper bar 52 shortens, (see FIG. 7) continuing to maintain the inlet in a closed position. As the hinges flex, upper bar 52 and lower bar 56 move closer to each other in accordian like fashion without breaking.

When the flow has stopped, and with the bottle at atmospheric pressure, the vacuum line is disconnected via the detachable vacuum fittings and also the hose from the patient to nipple 22 and the bottle removed from the support. By twisting cover 17, same can be removed from bottle 11 and the bottle emptied of drainage. The entire suction bottle assembly can then be sterilized or disposed of.

The float, bracket and valve combination detailed above provides automatic and positive control of drainage until the bottle has filled to approximately 1⅛ inches from the lip of the bottle at various negative pressures in an efficient and economical manner. By use of plastic and flexible components throughout, maintaining air tight connections can be easily and economically accomplished without special sealing material.

I claim:

1. A suction bottle assembly for effecting drainage from a patient, comprising:
   a. a bottle;
   b. a cover mounted on said bottle and providing an airtight seal therewith, said cover having an inlet means adapted to be connected to a source of vacuum and also in communication with the interior of said bottle, said cover having intake means adapted to be connected to a patient and which is also in communication with the interior of said bottle;
   c. a bracket means hingedly connected to the interior of said cover generally adjacent said inlet means:
   d. vacuum relief means located in said cover; and
   e. a float connected to said bracket, said float rising vertically as the drainage enters said bottle and moving said bracket to contact said vacuum inlet means to close same and to open said vacuum relief means.

2. The assembly of claim 1 in which said vacuum relief means is a valve extending outside said cover and also connected to said bracket, said bracket closing said valve on downward movement of said float.

3. The assembly of claim 2 in which said valve and bracket are constructed so that said valve is opened at substantially the same time as said vacuum inlet is closed.

4. The assembly of claim 3 in which said valve is located between the hinge connection of said bracket and said vacuum inlet means.

5. A suction bottle assembly for effecting drainage from a patient, comprising:
   a. a bottle;
   b. a cover mounted on said bottle and providing an airtight seal therewith, said cover having an inlet means adapted to be connected to a source of vacuum and also in communication with the interior of said bottle, said cover having intake means adapted to be connected to a patient and which is also in communication with the interior of said bottle;
   c. a parallel bar bracket hingedly connected to the interior of said cover generally adjacent said inlet means, said bracket including a pair of spaced, parallel bars and a member hingedly mounted therebetween;
   d. vacuum relief means located in said cover; and
   e. a float connected to said bracket, said float rising vertically as the drainage enters said bottle and moving said bracket to contact and fold about said vacuum inlet means to close same and to open said vacuum relief means.

6. The assembly of claim 5 in which said member is located more remote from said connection of said bracket with said cover than said inlet means and said float is mounted on said member.

7. The assembly of claim 6 in which said bracket has four hinges.

8. The assembly of claim 7 in which said float has an open bottom.

9. The assembly of claim 8 in which said float is of a greater size in direction transverse to said bracket than parallel to said bracket and said float is connected to said member so that the centerline of said float is generally adjacent the centerline of said bottle.

10. The assembly of claim 9 in which said bracket is integral and made of plastic material and has flexible hinges and a flexible cantilever sealing surface.

* * * * *